(12) United States Patent
Green et al.

(10) Patent No.: US 6,277,255 B1
(45) Date of Patent: Aug. 21, 2001

(54) ELECTROCHEMICAL SENSING CIRCUITS

(75) Inventors: Ian MacDonald Green, London; Michael Jackson, Berkshire, both of (GB)

(73) Assignee: Central Research Laboratories, Limited, Hayes (GB)

( * ) Notice: Subject to any disclaimer, the term of this patent is extended or adjusted under 35 U.S.C. 154(b) by 0 days.

(21) Appl. No.: 09/403,522
(22) PCT Filed: Apr. 29, 1998
(86) PCT No.: PCT/GB98/01252
§ 371 Date: Dec. 17, 1999
§ 102(e) Date: Dec. 17, 1999
(87) PCT Pub. No.: WO98/50789
PCT Pub. Date: Nov. 12, 1998

(30) Foreign Application Priority Data

May 1, 1997 (GB) .................................................. 9708786

(51) Int. Cl.[7] .................................................... G01N 27/26
(52) U.S. Cl. ......................... 204/406; 204/401; 204/412
(58) Field of Search .................................. 204/400, 406, 204/401, 412

(56) References Cited

U.S. PATENT DOCUMENTS 4,426,621 * 1/1984 Galwey et al. ...................... 324/439

* cited by examiner

*Primary Examiner*—T. Tung
*Assistant Examiner*—Alex Noguerola
(74) *Attorney, Agent, or Firm*—William H. Bollman

(57) ABSTRACT

An electrochemical cell sensing circuit for an electrochemical cell having a working electrode, a counter electrode and a reference electrode in an electrolyte, which in use, when a gas to be analysed is introduced into the cell, generating a current between the counter electrode and the working electrode, and a potential at a position in the electrolyte is sensed by the reference electrode. The circuit comprising power supply means (12, 13, 14, 15, 16, R4, R5, D1) for applying an offset voltage to the counter electrode (c) relative to the working electrode (w), an amplifier means (A3, A5) for monitoring the voltage difference between the reference electrode (r) and the working electrode (w) and operable in use to feed back a current to the working electrode (w) through a feed back loop, and thereby tend to maintain the working electrode (w) at substantially the same potential as the reference electrode (r), the circuit includes measuring means (15, 16, 17, S1, R3, C2, A3) for measuring the current feed back by the amplifier (A2, A3) to the working electrode (w) as a measure of the cell current flowing between the working electrode (w) and the counter electrode (c).

8 Claims, 1 Drawing Sheet

PRIOR ART CIRCUIT

ELECTROCHEMICAL SENSING CIRCUITS

BACKGROUND OF THE INVENTION

This invention relates to electrochemical sensing circuits and in particular to electrical circuits which sense cell current flow from a three terminal electrochemical cell.

Three terminal electrochemical cells are used for a variety of gas monitors and comprise a cell in which a gas to be analysed is introduced and three spaced apart electrodes. The three electrodes comprise a main pair across which the cell current is generated and a reference electrode which enables a potential at a predetermined point in the cell electrolyte measured. The cell current is proportional to the concentration of the compound or element being sensed by the cell, which may, for example, be carbon monoxide.

Known three-terminal electrochemical cells can be stabilised using the circuit shown in FIG. 1. In order to stabilise the cell, the "working" and "reference" electrodes, labelled "W" and "R" respectively must be brought to the same electrical potential. No current is taken from the reference electrode. Instead, current is injected into the counter electrode, labelled "C", by the amplifier A1 until both the reference and working electrodes, R and W respectively, are the same potential. The current which flows in both the counter and working electrodes is the cell current and due to the internal operation of the cell this is proportional to the concentration of the compound being sensed by the cell.

Referring to FIG. 1, the Amplifier, A1, maintains the reference electrode at 0V by feeding back current to the counter electrode. Amplifier A2 maintains the working electrode at 0V, since the negative input of amplifier A2 is at 0V. The cell current is driven by amplifier A1 but is sensed by amplifier A2, because the cell current passes through resistor R2 to develop the voltage V out.

A disadvantage of the prior known circuit shown in FIG. 1 is that it is prone to oscillation, because the virtual earth impedance of each amplifier appears as part of a feedback path of the other amplifier. This can lead to oscillation at high frequencies, where the virtual earth impedances are not well defined.

A second disadvantage, for low cost microcontroller-based applications, is that the output V out is an analogue voltage which must go through an analogue to digital conversion before it can be processed digitally.

A third disadvantage is that, whereas V out is normally positive when gas is being sensed, the counter electrode charges negatively, requiring the output of amplifier A1 to go negative. Therefore the circuit shown in FIG. 1 requires both positive and negative supplies (shown as V+ and V−).

A further cell which uses a potentiostat-type circuit is described in U.S. Pat. No. 4,048,041 (U.S. Army). The electronic circuit controls voltage potential applied to working electrodes of a three-electrode electrochemical cell. The electrochemical cell is incorporated into a sensor which operates by measuring the difference current between the cell's grounded anode and a negatively pulsed cathode. This circuit is quite complex, and requires both positive and negative supplies.

BRIEF SUMMARY OF INVENTION

An object of the present invention is to provide a simplified sensing circuit in which at least one of the above mentioned disadvantages is overcome, and which can be powered by an isolated DC supply, such as a battery.

According to one aspect of the present invention there is provided an electrochemical cell sensing circuit comprising an electrochemical cell having a working electrode, a counter electrode and a reference electrode in an electrolyte, the cell being constructed such that in use, when a gas to be analysed is introduced into the cell, a current flows between the counter electrode and the working electrode, and a potential at a position in the electrolyte is sensed by the reference electrode, the circuit further comprising power supply means for applying an offset voltage to the counter electrode relative to the working electrode, an amplifier means for monitoring the voltage difference between the reference electrode and the working electrode and operable in use to feed back a current to the working electrode through a feed back loop and thereby tend to maintain the working electrode at substantially the same potential as the reference electrode, and measuring means for measuring the current feed back by the amplifier to the working electrode as a measure of the cell current flowing between the working electrode and the counter electrode.

Preferably the measuring means comprises a resistor means in series connection between an output of the amplifier and the working electrode, and means are provided for measuring the voltage generated across the resistor.

Alternatively the measuring means comprises a capacitor connected in series between an output of the amplifier and the working electrode, a switch means connected in parallel across the capacitor, said switch being operable in a closed position to short out the capacitor and in an open position to allow the capacitor to be charged by the current feed back to the working electrode by the amplifier and a comparator adapted to receive, at a first input, the output of the amplifier, and at a second input, a reference voltage Vr, said comparator being operable to compare the first and second inputs and produce an output signal indicative of the cell current when said switch is open.

Preferably the power supply means comprises a DC supply which applies a positive potential to the counter electrode.

Preferably the amplifier is connected between a second DC supply which is isolated from the DC supply which applies to the positive potential to the counter electrode.

Preferably the said power supply means comprises a DC supply which applies a positive potential to the counter electrode and the comparator and amplifier are connected between a second DC supply which is isolated from the DC supply which applies the positive potential to the counter electrode.

The output signal from the comparator may be a digital signal. A means may be provided to inject a pulse in the supply to the counter electrode to provide a means of testing the correct operation of the circuit.

BRIEF DESCRIPTION OF THE DRAWINGS

Two embodiments of the present invention will now be described, by way of example, with reference to the accompanying drawings, in which.

DETAILED DESCRIPTION OF THE INVENTION

Figure 2:
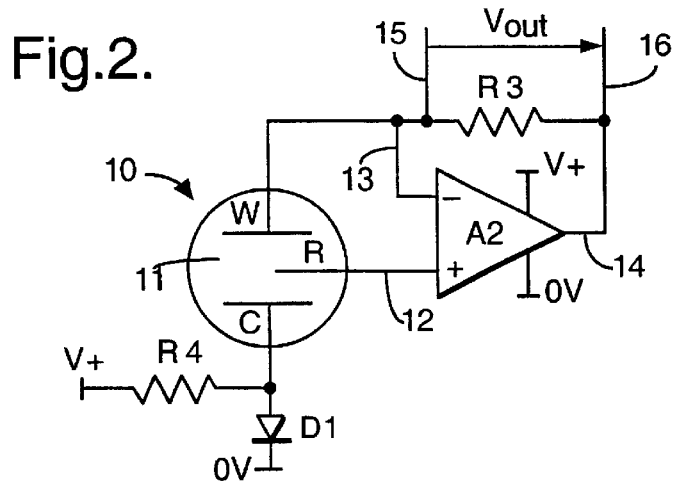
FIG. 2 illustrates one embodiment of the present invention.

Referring to FIG. 2, the electrochemical cell 10 is of conventional construction and comprises a chamber, or cavity 11 into which a gas to be monitored is introduced. Three spaced electrodes W, C, R are located in the cavity 11. Electrode R constitutes a reference electrode and is connected to an input 12 of an operational amplifier A2. A second input 13 of amplifier is connected to the electrode W. The output 14 of the amplifier A2 is connected to electrode W through a feedback loop which includes resistor R3. The counter electrode, C, is connected to a reference voltage generated by resistor R4 and diode D1 which is connected to the 0V line.

The amplifier A2 feeds back current through resistor R3 to maintain the working and reference electrodes, W and R respectively, at the same potential.

When gas is sensed by the cell 10, the output of amplifier A2 goes positive to deliver a positive current into the working electrode W, and at the same time, the electrode W charges positive with respect to the counter electrode C. These two effects ensure that the output amplifier A2 remains positive relative to the 0V line at all times.

The voltage across R3 is an accurate output which is proportional to gas concentration in the cell 10. If the +V supply is provided by an isolated battery (not shown), the terminals 15, 16 of the resistor R3 can be taken as the output with one terminal connected to an external isolated ground. Where accuracy is less important, it may be sufficient to sense the output of amplifier A2 relative to the 0V line, but the output voltage of amplifier A2 includes a component due to the offset voltage between the working electrode, W, and the counter electrode C. The offset is normally a very small fraction of a volt.

The offset voltage on the counter electrode, C, is generated by resistor R4 and diode D1 and protects those cells which would otherwise have an in-built tendency for the counter electrode to be positive relative to the working electrode. The offset voltage also allows for exposure to gases which would otherwise spuriously provoke a reverse response from the cell. If the cell is designed to have an inbuilt positive bias from the counter electrode, C, to the working electrode, W, it may not be necessary to impose an offset voltage on counter electrode C.

Figure 1:
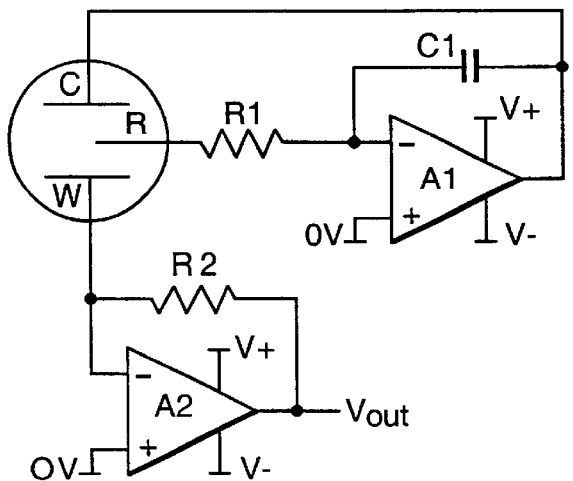
FIG. 1 illustrates a known electrochemical sensing circuit and is discussed above.

An experimental circuit based on FIG. 1 used a Maxim MAX 406 amplifier and R4 provided 1 $\mu$A into D1 from a 6 volt battery. R3 was 12 k$\Sigma$, to give the cell an output sensitivity of 1 mV/ppm of carbon monoxide sensed by the cell under test. The total current consumption was 3 $\mu$A which would provide a battery life of many years.

Figure 3:
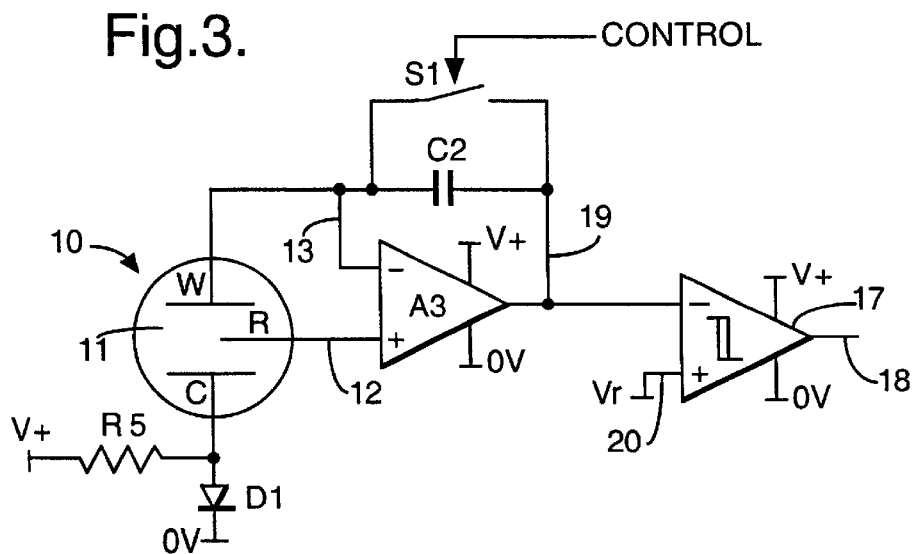
FIG. 3 illustrates a second embodiment of the present invention for converting the cell output into a timing signal.

FIG. 3 shows a further embodiment of the invention in which the output from the cell is converted into a timing signal. In FIG. 3 similar components to those shown in FIG. 2 are given the same reference numeral.

Referring in greater detail to FIG. 3 the amplifier A3 operates in very much the same way as amplifier A2 of FIG. 2 except that the cell current, instead of flowing through resistor R3, flows through switch S1 when the switch is closed, or through capacitor C2 when the switch S1 is open.

The output 16 of the amplifier A3 is connected to one input of a comparator 17 and a reference voltage Vr is applied to a second input of the comparator 17. The reference voltage may be provided by a separate circuit or could be a tapping on the resistor R5.

To measure the cell current, a switch S1 is first closed thereby shorting out capacitor C2. A timer (not shown) is started, and switch S1 is opened. The capacitor C2 then charges positively at a rate proportional to the cell current. The comparator 17 switches when the output voltage of the amplifier A3 equals the reference voltage Vr, thus producing a timing signal 18 representative of the cell current.

A sensor based on the circuit of FIG. 3 will suffer minor errors due to the voltage offset between the working electrode, W, and the counter electrode, C. If greater accuracy is required the reference voltage Vr can be made to vary with the working electrode voltage as buffered, for example, by an emitter follower.

What is claimed is:

1. An electromechanical cell sensing circuit comprising:
    an electromechanical cell having a working electrode, a counter electrode, a reference electrode and an electrolyte, said reference electrode sensing a potential at a position in said electrolyte when an introduction of gas to be analysed into said electromechanical cell provides a current flow between said counter electrode and said working electrode;
    a power supply having a pair of voltage rails at different potentials;
    biasing means for offsetting a potential of said counter electrode from one of said voltage rails;
    an amplifier to monitor a voltage difference between said reference electrode and said working electrode, and to apply a feedback current to said working electrode through a feedback loop to maintain said working electrode at substantially a same potential as said reference electrode; and
    a measurement circuit to monitor said feedback current as a measure of said current between said working electrode and said counter electrode.

2. The electrochemical cell sensing circuit according to claim 1, wherein said measurement circuit comprises:
    a resistor between an output of said amplifier and said working electrode; and
    at least one terminal allowing a voltage generated across said resistor to be measured therefrom.

3. The electrochemical cell sensing circuit according to claim 1, wherein said power supply comprises:
    a first direct current supply applying a positive potential to said counter electrode.

4. The electrochemical cell sensing circuit according to claim 3, wherein:
    said amplifier connects to a second direct current supply isolated from said first direct current supply.

5. The electrochemical cell sensing circuit according to claim 1, further comprising:
    testing means for testing a correct operation of said electrochemical sensing circuit by injecting a test pulse into said counter electrode.

6. An electromechanical cell sensing circuit comprising:
    an electromechanical cell having a working electrode, a counter electrode, a reference electrode and an electrolyte, said reference electrode sensing a potential at a position in said electrolyte when an introduction of gas to be analysed into said electromechanical cell provides a current flow between said counter electrode and said working electrode;
    a power supply applying an offset voltage to said counter electrode relative to said working electrode;
    an amplifier to monitor a voltage difference between said reference electrode and said working electrode, and to apply a feedback current to said working electrode through a feedback loop to maintain said working electrode at substantially a same potential as said reference electrode;
    a measurement circuit to monitor said feedback current as a measure of said current between said working electrode and said counter electrode;

a capacitor between an output of said amplifier means and said working electrode;

a switch in parallel across said capacitor, said switch shorting out said capacitor when said switch is in a closed position, and said switch allowing said feedback current to charge said capacitor when said switch is in an open position; and a comparator adapted to receive said output of said amplifier at a first input, and a reference voltage at a second input, said comparator comparing said first input and said second input to produce an output signal indicative of said cell current when said switch is in said open position.

7. The electrochemical cell sensing circuit according to claim 6, wherein said power supply comprises:

a first direct current supply applying a positive potential to said counter electrode; and a second direct current supply supplying power to said comparator and said amplifier, said second direct current supply being isolated from said first direct current supply.

8. The electrochemical cell sensing circuit according to claim 7, wherein:

said output signal is a digital signal.

\* \* \* \* \*